United States Patent [19]
Viera

[11] Patent Number: 5,411,033
[45] Date of Patent: May 2, 1995

[54] ATHERECTOMY GUIDEWIRE

[75] Inventor: Fernando M. Viera, Hialeah, Fla.

[73] Assignee: Cordis Corporation, Miami Lakes, Fla.

[21] Appl. No.: 166,693

[22] Filed: Dec. 14, 1993

[51] Int. Cl.$^6$ .............................................. A61B 6/00
[52] U.S. Cl. .................... 128/772; 128/657; 606/170
[58] Field of Search ............... 128/657, 772; 606/205, 606/206, 170; 604/95, 270, 280, 282

[56] References Cited

U.S. PATENT DOCUMENTS

| | | | |
|---|---|---|---|
| 3,906,938 | 9/1975 | Fleischhacker | 128/772 |
| 4,796,642 | 1/1989 | Harris | 128/657 X |
| 4,846,186 | 7/1989 | Box et al. | |
| 5,106,381 | 4/1992 | Chikaua | 128/772 X |
| 5,170,787 | 12/1992 | Lindegren | 128/772 X |
| 5,211,652 | 5/1993 | Derbyshire | 606/206 X |
| 5,267,574 | 12/1993 | Viera et al. | 128/772 |
| 5,282,817 | 2/1994 | Hoogeboom et al. | 606/205 X |

*Primary Examiner*—Sam Rimell
*Attorney, Agent, or Firm*—Gerstman, Ellis & McMillin, Ltd.

[57] ABSTRACT

A guidewire for insertion into the vascular system of a patient, to provide a path of advancement for an atherectomy catheter which surrounds the guidewire as it advances. The guidewire has an intermediate portion positioned proximally of the distal tip, which intermediate portion defines a transversely enlarged portion of a size to prevent substantial distal advancement of the atherectomy catheter or other catheter that surrounds the guidewire. Particularly, this protects the distal tip portion of the guidewire from engagement with moving blades of an atherectomy catheter.

13 Claims, 1 Drawing Sheet

ATHERECTOMY GUIDEWIRE

BACKGROUND OF THE INVENTION

Atherectomy devices of various kinds have been used to break up and remove stenoses formed on the inner walls of the arteries of patients, particularly the coronary arteries. Some of these devices comprise catheters having rotary blades or the like on their distal end to cut through the stenosis and then, typically, to remove the stenosis through the lumen of the catheter, or by some other means.

Such atherectomy devices have typically been advanced along a guidewire in a manner that is similar in broad scope to the advancement of an angioplasty balloon catheter along a guidewire, in which the balloon is used to expand stenoses in arteries to improve the flow of blood therethrough. However, the current guidewires which are used with atherectomy devices having a distal, movable blade for cutting are lacking in handling characteristics, particularly torquability and steerability, which renders them more difficult to advance into narrow, convoluted arteries, particularly the coronary arteries which often are of that type. One reason for this is that many conventional designs of high torquability and high steerability guidewire cannot be safely used with a moving blade atherectomy device. Such known guidewires have a distal spring surrounding a distal tip end portion of the guidewire. Such guidewire should not be used with moving blade atherectomy devices, because of the danger that the moving blade may engage the guidewire spring within a patient's artery, with the potential for serious injury to the patient.

In accordance with this invention, a guidewire for an atherectomy device having a moving blade, specifically a rotary blade, is provided in which the guidewire may have state of the art torquability and steerability, making use of a distal spring as is conventional in some of the best guidewire designs. At the same time, the atherectomy device is prevented from advancing along the guidewire to such a degree that its moving blade can engage the guidewire spring.

Thus, the atherectomy device can be used by the physician with confidence that the atherectomy device will not engage a distal guidewire spring. Such a guidewire thus provides excellent torquability and steerability for access to narrow, occluded, convoluted arteries which cannot be reached by conventional atherectomy device guidewires. At the same time, the device is safe with respect to the blade engaging a guidewire distal spring or similar item. The physician does not need to worry at all about that risk, and thus is free to concentrate upon other aspects of the procedure.

DESCRIPTION OF THE INVENTION

In accordance with this invention a guidewire is provided, typically for insertion into the vascular system of a patient. The guidewire comprises a main wire body, a distal tip portion, and an intermediate portion positioned proximally of the distal tip portion. The intermediate portion defines a transversely enlarged guidewire portion which is of a size to prevent substantial distal advancement of a tubular sleeve member, such as an atherectomy catheter that surrounds the guidewire, beyond the intermediate guidewire portion.

The transversely enlarged guidewire portion is typically flattened in one transverse dimension and widened in the other transverse dimension relative to portions of the guidewire which are proximal to the transversely enlarged portion. However, other configurations which provide a transversely enlarged guidewire portion may be used. For example, the guidewire may be enlarged in the form of a bulb or ball for similar effect. It may be of X or Y shaped transversely enlarged cross-section at the intermediate portion, or any other desired geometry having similar effect, to prevent distal advancement of the tubular sleeve member surrounding the guidewire.

Thus, the distal tip portion of the guidewire may carry a helical spring surrounding the rest of the guidewire in accordance with state of the art designs which provide excellent trackability and torquability, for the best available capability for entry into small, convoluted arteries. Preferably, the helical spring has a proximal end which is no more than one inch from the transversely enlarged guidewire portion.

DESCRIPTION OF SPECIFIC EMBODIMENTS

Figure 1:
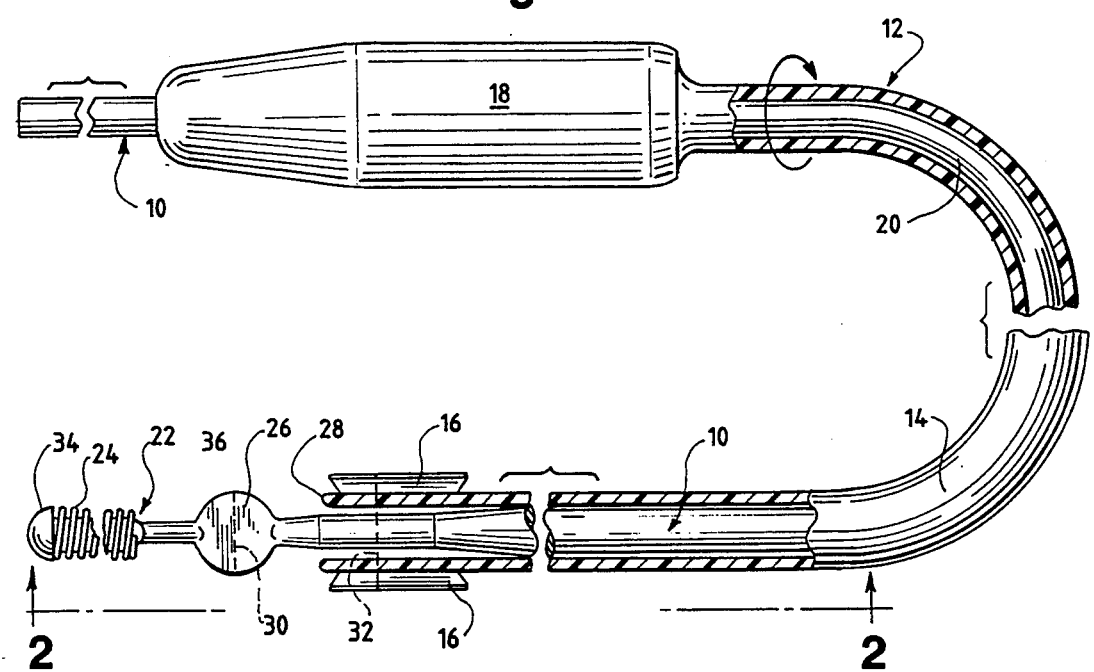
FIG. 1 is a plan view, with portions broken away and taken partly in section, of a guidewire made in accordance with this invention, surrounded in sliding relation with an atherectomy catheter.
Figure 2:
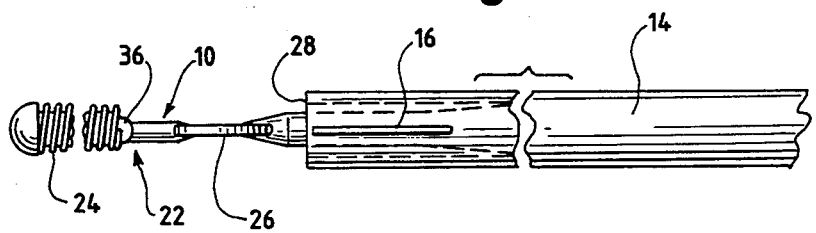
FIG. 2 is an elevational view along line 2—2 of FIG. 1 of the distal end of the guidewire and atherectomy catheter.

Referring to the drawings, a guidewire 10 is disclosed, being proportioned for insertion by a conventional surgical procedure into coronary arteries for coronary atherectomy procedures. Guidewire 10 is surrounded by a conventional atherectomy catheter 12, which comprises a flexible catheter tube 14, a distal cutter blade assembly 16 carried by catheter tube 14, and a proximal motor 18 for rotating catheter tube 14 and cutter blade assembly 16, to obtain cutting action against arterial stenoses.

Guidewire 10 comprises a main wire body 20, connected to a distal tip portion 22, which is shown to carry helical spring 24 in a relation surrounding the guidewire, to provide in known manner excellent control of the guidewire. Such a guidewire can go around relatively sharp corners in the coronary arterial system with excellent control for passing through the arteries to a desired destination.

When the distal end of guidewire 10 has reached the desired destination of a stenosis, it may be advanced somewhat beyond the point where the atherectomy is desired, so that the rotating blades 16 of catheter 14 may engage the stenosis. Then, motor 18 may be activated, to cause catheter 14 and blades 16 to rotate in conventional manner, to break loose the undesired stenotic material and to remove it in a known manner of the prior art not dealt with here in detail.

However, as previously discussed, it is important to be sure that rotating blades 16 do not enter into engagement with distal spring 24 of the guidewire as catheter 12 advances along guidewire 10. To this end, guidewire 10 defines an intermediate portion which in this embodiment defines a transversely enlarged, flat section 26. Flat section 26 can be simply made from guidewire by a stamping process, causing the ductile metal of the guidewire to flow outwardly into a flattened shape, as shown.

The maximum width of guidewire portion 26 should be greater than the maximum diameter of portions of guidewire 10 which are proximal to portion 26, so that the distal end 28 of catheter 12 is of a lesser inner diameter than the maximum transverse dimension 30 of flattened, intermediate guidewire portion 26. Thus, it becomes impossible for catheter 12 to advance beyond the position where its distal end 28 enters into engagement with flattened guidewire portion 26, thus effectively terminating the forward advancement of catheter 12 along guidewire 10. Because of this, rotary blades 16 cannot enter into engagement with guidewire spring 24 under any normal condition of use of the system.

This permits the physician to perform the atherectomy procedure without giving any consideration to the risk of overadvancement of catheter 12 relative to guidewire 10, because that particular risk of the procedure is eliminated when an atherectomy catheter 12 is used in conjunction with a guidewire 10, in which the transverse dimension 30 of intermediate portion 26 exceeds the inner diameter of the catheter at distal end 28. For example, for a typical guidewire in which the main portion of wire body 20 may have a maximum diameter of about 0.008 inch to 0.011 inch. Maximum dimension 30 may exceed that diameter and may be 0.010 inch to 0.025 inch, with a thickness perpendicular to the diameter 30 of about 0.001 to 0.005 inch. Preferably, dimension 30 is of less dimension than the cutting diameter 32 of blades 16, for example 0.011 or 0.012 inch.

Helical spring 24 is shown to be constrained between a distal tip 34 and a bond 36 of guidewire 10. The proximal end of spring 24 is preferably positioned within an inch of the distal end of transversely enlarged guidewire portion 26.

Thus, atherectomy can be performed in which the atherectomy catheter tracks through the arterial system of a patient, as guided by guidewire 10, which can take advantage of the best, state-of-the-art characteristics for steerability and torquability, among other advantages. Nevertheless, the rotating blades of the atherectomy catheter are reliably kept away from the distal coil 24, found in many of such advantageous guidewires.

The above has been offered for illustrative purposes only, and is not intended to limit the scope of the invention of this application, which is defined in the claims below.

That which is claimed is:

1. A guidewire for guiding a catheter having an internal diameter, said guidewire being adapted for insertion into the vascular system of a patient, said guidewire comprising:
   a main wire body having a distal tip portion including a coil;
   an intermediate portion positioned proximally of said distal tip portion;
   said intermediate portion defining a transversely enlarged guidewire portion proximally of the coil of a size that is greater than said internal diameter, to prevent substantial distal advancement, beyond said intermediate portion, of the catheter.

2. The guidewire of claim 1 in which said transversely enlarged guidewire portion is flattened in one transverse dimension and widened in the other transverse dimension relative to portions of said guidewire which are proximal to said transversely enlarged portion.

3. The guidewire of claim 1 which is surrounded in sliding relation by an atherectomy catheter.

4. The guidewire of claim 1 in which said coil has a proximal end which is no more than one inch longitudinally from said transversely enlarged guidewire portion.

5. A guidewire for insertion into the vascular system of a patient, which comprises: a main wire body having a distal tip portion, and an intermediate portion positioned proximally of said distal tip portion, said intermediate portion defining a transversely enlarged guidewire portion which is flattened in one transverse dimension and widened in the other transverse dimension relative to portions of said guidewire which are proximal to said transversely enlarged portion, said transversely enlarged guidewire portion having a maximum width that is greater than the internal diameter of a catheter that surrounds the guidewire to prevent substantial distal advancement beyond the intermediate portion of said catheter, said distal tip portion carrying a helical spring surrounding said guidewire.

6. The guidewire of claim 5 in which said helical spring has a proximal end which is no more than one inch longitudinally from said transversely enlarged guidewire portion.

7. The guidewire of claim 6 which is surrounded in sliding relation by an atherectomy catheter.

8. A guidewire for insertion into the vascular system of a patient, said guidewire being surrounded in sliding relation by an atherectomy catheter having an internal diameter, said guidewire comprising: a main wire body having a distal tip portion, and an intermediate portion positioned proximally of the distal tip portion, said intermediate portion being flattened in one transverse dimension and widened in the other transverse dimension relative to portions of said guidewire which are proximal to said transversely enlarged portion, to define a transversely enlarged guidewire portion of a size that is greater than said internal diameter to prevent substantial distal advancement of said atherectomy catheter beyond said intermediate portion.

9. The combination of a guidewire and atherectomy catheter of claim 8 in which the distal tip portion of said guidewire carries a coil surrounding said guidewire.

10. The combination of a guidewire and atherectomy catheter of claim 9 in which said atherectomy catheter defines cutting blades adjacent the distal end of said catheter, said cutting blades defining a rotational outer diameter, said catheter also defining at said distal end a lumen, the maximum transverse dimension of said guidewire intermediate portion being greater than the internal diameter of said lumen.

11. The combination of a guidewire and atherectomy catheter of claim 10 in which the maximum transverse dimension of said guidewire intermediate portion is less than the rotational outer diameter.

12. The combination of a guidewire and atherectomy catheter of claim 9 in which said atherectomy catheter defines cutting blades adjacent the distal end of said catheter, said cutting blades defining a rotational outer diameter, said catheter also defining at said distal end a lumen, the maximum transverse dimension of said guidewire intermediate portion being greater than the internal diameter of said lumen.

13. The combination of a guidewire and atherectomy catheter of claim 12 in which the maximum transverse dimension of said guidewire intermediate portion is less than the rotational outer diameter.

* * * * *